United States Patent [19]

Martal et al.

[11] Patent Number: 5,378,823
[45] Date of Patent: Jan. 3, 1995

US005378823A

[54] NUCLEIC ACIDS ENCODING TYPE I INTERFERON VARIANTS

[75] Inventors: Jacques Martal, Jouy-en-Josas; Erich DeGryse, Strasbourg; Pierre Gaye; Madia Charlier, both of Paris; Gilles Charpigny, Orleans; Pierrette Reinaud, Chatillon; Gérard Chaouat, Paris, all of France

[73] Assignee: Institut National de la Recherche Agronomique-I.N.R.A., Paris, France

[21] Appl. No.: 915,707

[22] PCT Filed: Nov. 29, 1991

[86] PCT No.: PCT/FR91/00953
§ 371 Date: Sep. 11, 1992
§ 102(e) Date: Sep. 11, 1992

[87] PCT Pub. No.: WO92/09691
PCT Pub. Date: Jun. 11, 1992

[30] Foreign Application Priority Data

Nov. 29, 1990 [FR] France ................................ 90 14945
Nov. 29, 1990 [FR] France ................................ 90 14946

[51] Int. Cl.$^6$ ............................................. C07H 21/04
[52] U.S. Cl. .................................. 536/23.52; 530/351; 435/69.51; 435/320.1; 935/10
[58] Field of Search ............... 530/407, 351; 424/85.4, 424/85.7; 435/69.51, 69.7, 69.8, 69.9, 172.1, 320.1, 252.3; 536/23.52; 935/10, 37, 48, 69

[56] References Cited

U.S. PATENT DOCUMENTS 4,782,139 11/1988 DiMarchi et al. .................. 530/407

FOREIGN PATENT DOCUMENTS

| 8932953 | 10/1989 | Australia . |
| 088632 | 9/1983 | European Pat. Off. . |
| 123544 | 10/1984 | European Pat. Off. . |
| 220958 | 5/1987 | European Pat. Off. . |
| WO84/00776 | 3/1984 | WIPO . |
| WO89/08706 | 9/1989 | WIPO . |
| WO90/09806 | 9/1990 | WIPO . |

OTHER PUBLICATIONS

E. Degryse et al. Gene 118:47–53 1992.
I. Palva et al., "Secretion of Interferon by *Bacillus subtilis*", *Gene*, vol. 22, 1983, pp. 229–235.
K. M. Zsebo et al., "Protein Secretion from *Saccharomyces cerevisiae* Direction by the Prepro-α-factor Leader Region", *The Journal of Biological Chemistry*, vol. 261, No. 12, May 5, 1986, pp. 5858–5865.

Primary Examiner—Garnette D. Draper
Assistant Examiner—L. Spector
Attorney, Agent, or Firm—Bell, Seltzer, Park & Gibson

[57] ABSTRACT

Variants of type I interferons containing peptide extensions, and their production using recombinant DNA techniques, are described. Expression cassettes comprising DNA coding for the variant interferon, DNA coding for a signal peptide, and a promoter are described for use in transforming yeast and in the production of the variant interferons.

5 Claims, 9 Drawing Sheets

| | | | | | | | | | | | | | | |
|---|---|---|---|---|---|---|---|---|---|---|---|---|---|---|
| ATG | GCC | TTC | GTG | CTC | TCT | CTA | CTG | ATG | GCC | CTG | GTG | CTG | GTC | 42 |
| Met | Ala | Phe | Val | Leu | Ser | Leu | Leu | Met | Ala | Leu | Val | Leu | Val | |
| -23 | | -20 | | | | | | -15 | | | | | -10 | |
| AGC | TAT | GGC | CCA | GGA | GGA | TCT | CTG | GGT | TGT | TAC | CTA | TCT | CAG | 84 |
| Ser | Tyr | Gly | Pro | Gly | Gly | Ser | Leu | Gly | Cys | Tyr | Leu | Ser | R5 | |
| | | | | -5 | | | | -1 | 1 | | | | 5 | |
| AGA | CTC | ATG | CTG | GAT | GCC | AGG | GAG | AAC | CTC | AAG | CTC | CTG | GAC | 126 |
| R6 | Leu | Met | Leu | Asp | Ala | Arg | Glu | Asn | Leu | Lys | Leu | Leu | Asp | |
| | | | | 10 | | | | | 15 | | | | | |
| CGA | ATG | AAC | AGA | CTC | TCC | CCT | CAT | TCC | TGT | CTG | CAG | GAC | AGA | 168 |
| Arg | Met | Asn | Arg | Leu | Ser | Pro | His | Ser | Cys | Leu | Gln | Asp | Arg | |
| 20 | | | | | 25 | | | | | 30 | | | | |
| AAA | GAC | TTT | GGT | CTT | CCC | CAG | GAG | ATG | GTG | GAG | GGC | GAC | CAG | 210 |
| Lys | R35 | Phe | Gly | Leu | Pro | Gln | Glu | Met | Val | R44 | Gly | Asp | Gln | |
| 35 | | | | | 40 | | | | | 45 | | | | |
| CTC | CAG | AAG | GAC | CAG | GCC | TTC | CCT | GTG | CTC | TAC | GAG | ATG | CTC | 252 |
| R48 | R49 | Lys | Asp | Gln | Ala | Phe | Pro | Val | Leu | Tyr | Glu | Met | Leu | |
| | | 50 | | | | | 55 | | | | | 60 | | |
| CAG | CAG | AGC | TTC | AAC | CTC | TTC | TAC | ACA | GAG | CAC | TCC | TCT | GCT | 294 |
| Gln | Gln | Ser | Phe | Asn | Leu | Phe | Tyr | Thr | Glu | His | Ser | Ser | Ala | |
| | | | 65 | | | | | 70 | | | | | 75 | |
| GCC | TGG | GAC | ACC | ACC | CTC | CTG | GAC | CAG | CTC | TGC | ACT | GGA | CTC | 336 |
| Ala | Trp | Asp | Thr | Thr | Leu | Leu | Asp | Gln | Leu | Cys | Thr | Gly | Leu | |
| | | | | 80 | | | | | 85 | | | | | |
| CAA | CAG | CAG | CTG | GAC | CAC | CTG | GAC | ACC | TGC | AGG | GGT | CAA | GTG | 378 |
| Gln | Gln | Gln | Leu | Asp | His | Leu | Asp | Thr | Cys | Arg | Gly | Gln | Val | |
| 90 | | | | | 95 | | | | | 100 | | | | |
| ATG | GGA | GAG | GAA | GAC | TCT | GAA | CTG | GGT | AAC | ATG | GAC | CCC | ATT | 420 |
| Met | Gly | Glu | Glu | Asp | Ser | Glu | Leu | Gly | Asn | Met | Asp | Pro | Ile | |
| | 105 | | | | | 110 | | | | | 115 | | | |
| GTG | ACC | GTG | AAG | AAG | TAC | TTC | CAG | GGC | ATC | TAT | GAC | TAC | CTG | 462 |
| Val | Thr | Val | Lys | Lys | Tyr | Phe | Gln | Gly | Ile | Tyr | Asp | Tyr | Leu | |
| | | 120 | | | | | 125 | | | | | 130 | | |
| CAA | GAG | AAG | GGA | TAC | AGC | GAC | TGC | GCC | TGG | GAA | ATC | GTC | AGA | 504 |
| Gln | Glu | Lys | Gly | Tyr | Ser | Asp | Cys | Ala | Trp | Glu | Ile | Val | Arg | |
| | | | 135 | | | | | 140 | | | | | 145 | |
| GTC | GAG | ATG | ATG | AGA | GCC | CTC | ACT | GTA | TCA | ACC | ACC | TTG | CAA | 546 |
| Val | Glu | Met | Met | Arg | Ala | Leu | Thr | Val | Ser | Thr | Thr | Leu | Gln | |
| | | | | 150 | | | | | 155 | | | | | |
| AAA | AGG | TTA | ACA | AAG | ATG | GGT | GGA | GAT | CTG | AAC | TCA | CCT | TGA | 588 |
| Lys | Arg | Leu | Thr | Lys | Met | Gly | Gly | Asp | Leu | Asn | Ser | Pro | Ter | |
| 160 | | | | | 165 | | | | | 170 | | | | |

FIG. 1.

NUCLEIC ACIDS ENCODING TYPE I INTERFERON VARIANTS

BACKGROUND OF THE INVENTION

The present invention relates to new variants derived from type I interferons, obtained from yeast by recombinant DNA techniques.

Interferons were originally identified by their capacity for preventing viral replication. They constitute a family of proteins which have been divided into different groups. The classification currently proposed for interferons distinguishes two main types:

type I which groups together α, ω and β interferons and trophoblastins;

and type II which comprises γ interferons. α and ω interferons were previously known under the respective names α-I interferon (class I α) and α-II interferon (class II α), and trophoblastins could have been classified among the α-III interferons.

Apart from their antiviral activity, interferons can possess other functions. For example, it has already been established that, in some mammals such as cattle and sheep, trophoblastin participates in the phenomenon of maternal recognition of gestation.

Ovine trophoblastin or oTP has been demonstrated, respectively, by MARTAL et al. [J. Reprod. Fert., 56, 63-73 (1979); Pro. 10th intern. Congress on Anim. Reprod. and A.I., Urbana-Champaign (USA), 11, 509 (short communication) 1984)] and GODKIN et al. [J. Reprod. Fert., 65, 141-150 (1982)] in sheep, where it is produced in abundance by the embryo between the 12th and the 21st day of gestation; in cattle, it is produced between the 16th and the 24th day. It exists in at least 5 isoforms corresponding to different alleles. These isofoms are described in the international PCT application published under No. WO 89/08,706 in the name of the INSTITUT NATIONAL DE LA RECHERCHE AGRONOMIQUE. The molecular weight of trophoblastin is 20 kDa and its isoelectric point is between 5.3 and 5.5, depending on the isoform in question. Trophoblastins have been best characterized in certain ruminants. However, recent studies show that trophoblastin-like molecules also appear to exist in other mammals (horse, rabbit) and in man.

The trophoblastin produced by embryos possesses like the other interferons, miscellaneous biological activities.

Trophoblastin participates, in particular, in the mechanism of recognition of the embryo by the maternal body.

In most cases, the length of a gestation period greatly exceeds that of the luteal phase of the ovarian cycle. When fertilization has taken place, certain mechanisms occur in order to prolong the life of the corpus luteum and to prevent a return of the ovarian cycle. In ruminants, the embryo emits a biochemical signal in the form of trophoblastin (oTP). This substance enables the body to continue to secrete progesterone, a hormone which is essential eryonic for normal embryonic development.

GODKIN et al. [J. Reprod. Fert., 71, 57-64 (1984)] have shown that the intrauterine injection of purified oTP prolongs the secretion of luteal progesterone for a few days in recipient cycling ewes. FINCHER et al. [J. Reprod. Fert., 76, 425-433 (1986)] have found that the injection of natural oTP into the uterus delays oxytocin- or estradiol-induced luteolysis by several days and is accompanied by a reduction in prostaglandin $F_{2\alpha}$ secretion. Similar observations have been made with recombinant class I α interferons [PLANTE et al., Endocrinology 122, 2342-2344, (1988); STEWART et al., (1989) J. Repr. Fert. Supp. p. 127-138].

Trophoblastin is secreted by the embryo only during a relatively short period: from the 16th to the 24th day of gestation as regards cattle and from the 12th to the 22nd day of gestation in the case of sheep.

If the mother and the embryo are asynchronous, that is to say if the embryo secretes trophoblastin before the mother is physiologically capable of being sensitive thereto and of responding to such a stimulation, the corpus luteum regresses and the embryo dies. This possibility is especially critical when embryo transfer is being undertaken. To date, the failure rate in embryo transfer is greater than 30%. This is especially disastrous from an economic standpoint, the situation being still more marked in the case of in vitro fertilization.

A large number of embryonic mortalities are considered to be due to the fact that the state of development of the embryo and the maternal physiological conditions do not appear to be "in phase" at the time of implantation of the embryo in the uterus of the carrying mother. In addition, embryos are often frozen before transfer, resulting in the loss of some capacity for production of trophoblastin produced by the embryos.

An antiviral activity of trophoblastin has also been demonstrated, for example by MARTAL et al. [J. Reprod. Fert. Abs. series, 2, 3, (1988)] and PONTZER et al., [Biochem. Biophys. Res. Com., 152, 801-807, (1988)], as well as in the abovementioned PCT Application 89/08,706. This application also proposes the use of trophoblastin for preventing the rejection of organ transplants.

These properties enable a large number of therapeutic uses of trophoblastin to be envisaged. The development of such applications has, however, come up against the fact that trophoblastin could be obtained only from concept uses, which meant that it could not be produced in sufficient quantities for in vivo use.

In view of the foregoing, it would hence be very advantageous to have large quantities of trophoblastin available, in order to be able to treat animals at the start of gestation. Only recombinant DNA techniques can enable this objective to be achieved.

The cloning in *E. coli* of the complementary DNA (cDNA) of the messenger RNA (mRNA) coding for ovine trophoblastin has been described in PCT Application 89/08,706, mentioned above. The construction, from this cDNA, of chimeric genes enabling trophoblastin to be produced in microorganisms could hence be envisaged.

Nevertheless, the first attempts at expression of a cDNA coding for ovine trophoblastin proved inconclusive. These first attempts employed bacteria (*E. coli*) or yeasts (*S. cerevisiae*). In particular, an expression cassette intended for production of ovine trophoblastin in yeast, and comprising a DNA fragment coding for a signal peptide linked to the 5' end of the cDNA coding for mature ovine trophoblastin, did not enable synthesis to be obtained at an adequate level.

Moreover, ZSEBO et al., [J. Biol. Chem. 261 (13): 5858, (1986)] report that an α interferon cannot be secreted under good conditions and in large quantities using the "prepro" system of the α factor.

In addition, generally speaking, type I interferons are characterized by the presence of four cysteine residues at positions 1, 29, 99 and 139 which link with one another to form the disulfide bridges cys1-cys99 and cys29-cys139, and it is considered that the cysteine residue at the N-terminal position is essential for the maintenance of a correct conformational structure.

Surprisingly, the inventors have now found the addition of a DNA fragment coding for an additional amino acid, or for a di- or tripeptide such as, for example, for the dipeptide Ala-Pro or Ala-Gly, at the 5' end of the cDNA of an interferon possessing a cysteine at the N-terminal position to be beneficial. In effect, the whole of the coding structure is adequately expressed in yeast, and the variants thereby produced are secreted in larger quantities than those encoded by a structure lacking this fragment. Furthermore, it could be established that the variants obtained in this manner retain a biological activity similar to that of natural interferons. For example, the addition of a dipeptide at the N-terminal end of ovine trophoblastin gives rise to variants which retain the antiviral, immunological and antiluteolytic activities of natural trophoblastin.

SUMMARY OF THE INVENTION

Consequently, the invention proposes new variants of type I interferon, corresponding to one of the following formulae:

$$X_1-R_0 \qquad (I)$$

or alternatively $$X_1-X_2-R_0 \qquad (II)$$

or alternatively $$X_1-X_2-X_3-R_0 \qquad (III)$$

in which $X_1$, $X_2$ and $X_3$ are identical or different and each represent an amino acid,
and $R_0$ represents the amino acid sequence of the mature form of a type I interferon.

Preferably, $X_1$, $X_2$ and $X_3$ each represent an acidic amino acid, a basic amino acid or an amino acid chosen from the group consisting of alanine, valine, proline, glycine, serine, threonine, cysteine, asparagine and glutamine,
and $X_1$ represents an amino acid other than proline.

Type I interferon is understood, in particular, to mean an α interferon (IFN-αI) or ω interferon (IFN-αII) or a trophoblastin. An α interferon is characterized by a sequence of 166 amino acids, while an ω interferon possesses a C-terminal extension of 6 amino acids.

For a given species, the interferons generally exhibit some degree of natural allelic variety. For example, as regards the α interferons of human origin, at least about 15 genes are known, the coding sequences of which exhibit more than an 85% homology with one another.

Advantageously, a variant according to the invention corresponds to one of the formulae:

$$\text{Ala-Pro-}R_0' \qquad (IV)$$

or $$\text{Ala-Gly-}R_0' \qquad (V)$$

in which $R_0'$ represents the amino acid sequence of the mature form of an ω interferon or of a trophoblastin. Preferably, a variant according to the invention corresponds to one of the formulae:

$$\text{Ala-Pro-}R_0'' \qquad (VI)$$

or $$\text{Ala-Gly-}R_0'' \qquad (VII)$$

in which $R_0''$ represents the amino acid sequence of the mature form of an ω interferon or of a trophoblastin of bovine or ovine origin.

As an absolute preference, a variant according to the invention is of formula:

$$\text{Ala-Pro-}R_0''' \qquad (VIII)$$

or $$\text{Ala-Gly-}R_0''' \qquad (IX)$$

in which $R_0'''$ represents the amino acid sequence of the mature form of any one of the isoforms of ovine trophoblastin.

Isoforms of ovine trophoblastin designated T1, T2, T3, T4 and T5, respectively, are described in PCT Application 89/08,706.

In the context of the present invention, the preferred variants of formula (VIII) or (IX) include variants in which $R_0'''$ represents the amino acid sequence of the mature form of any one of the isoforms T1 to T5 of ovine trophoblastin.

FIG. 1 gives, as an example, the amino acid sequence of isoforms of trophoblastin, beginning with the cysteine residue at position 1 and ending with the proline residue at position 172 (signal peptide from -23 to -1), in which:

$R_5$ is a glutamic acid, glutamine or arginine residue,
$R_6$ is an arginine or lysine residue,
$R_{35}$ is a lysine or aspartic acid residue,
$R_{44}$ is a glutamic acid or aspartic acid residue,
$R_{48}$ is a leucine or aspartic acid residue, and
$R_{49}$ is a leucine or glutamine residue.

Preferred variants falling within the definition of the formulae (VIII) and (IX) include:
a variant of formula (Xa) in which $R_5$ is an arginine residue, $R_6$ is a lysine residue, $R_{35}$ is an aspartic acid residue, $R_{44}$ is a glutamic acid residue, $R_{48}$ is a leucine residue and $R_{49}$ a glutamine residue,
a variant of formula (Xb) in which $R_5$ is a glutamic acid residue, $R_6$ is an arginine residue, $R_{35}$ is a lysine residue, $R_{44}$ is a glutamic acid residue, $R_{48}$ is an aspartic acid residue and $R_{49}$ a leucine residue,
a variant of formula (Xc) in which $R_5$ is a glutamine residue, $R_6$ is an arginine residue, $R_{35}$ is an aspartic acid residue and $R_{44}$ is an aspartic acid residue, and
a variant of formula (Xd) in which $R_5$ is a glutamine residue, $R_6$ is an arginine residue, $R_{35}$ is an aspartic acid residue, $R_{44}$ is a glutamic acid residue, $R_{48}$ is a leucine residue and $R_{49}$ a glutamine residue.

Moreover, the subject of the invention is also a cassette for the expression of a variant according to the invention, which comprises at least:
a first DNA fragment coding for a variant according to the invention,
a second DNA fragment coding for a signal peptide, said second DNA fragment being linked to the 5' end of the first DNA fragment,
a promoter enabling said DNA fragments to be expressed in yeast.

Such a cassette is capable of promoting the expression of a peptide precursor consisting of a signal peptide on the N-terminal side, and a variant according to the invention on the C-terminal side. During passage through the endoplasmic reticulum, the signal peptide will be removed by cleavage to release the variant in mature form.

For use in an expression cassette according to the invention, said second DNA fragment is such that it can code for any signal peptide whose C-terminal end constitutes a proteolysis site capable of being recognized by a signal peptidase of the host organism which is to harbor the expression cassette. The signal peptidase must necessarily cut the C-terminal end of the signal peptide.

In the context of the present invention, advantageous signal peptides include, for example:
  the signal peptide of the precursor of the α factor having the amino acid sequence Met-Arg-Phe-Pro-Ser-Ile-Phe-Thr-Ala-Val-Leu-Phe-Ala-Ala-Ser-Ser-Ala-Leu-Ala (the proteolysis site is underlined);
  the signal peptide of the precursor of yeast β-1,3-glucanase having the amino acid sequence Met-Arg-Phe-Ser-Thr-Thr-Leu-Ala-Thr-Ala-Ala-Thr-Ala-Leu-Phe-Phe-Thr-Ala-Ser-Gln-Val-Ser-Ala (the proteolysis site is underlined); as well as the functional derivatives of these peptides.

For example, functional derivatives of the signal peptide of the precursor of β-1,3-glucanase are described in the PCT application File No. FR90/00,306 of 27.04.90.

Generally speaking, the promoter intended for the expression of the precursor of a variant according to the invention can be any promoter which is functional in yeast, preferably a promoter capable of inducing a good level of expression of any coding sequence. An advantageous promoter is, for example, the promoter of the MFα1 gene which codes for the α factor, or a functional derivative of this promoter.

Lastly, the subject of the invention is also:
  a yeast cell transformed with an expression cassette according to the invention, and
  a method for producing a variant according to the invention, which comprises the act of culturing a yeast cell transformed with an expression cassette according to the invention and of harvesting said variant from the culture supernatant.

The expression cassette according to the invention, as present in the transformed yeast cell, may be either incorporated in the genome of the yeast or carried by a plasmid capable of replicating in the yeast. In the latter case, it is appropriate to choose a plasmid/yeast host system such that the plasmid can be maintained in the yeast by selection pressure. An advantageous choice is of, on the one hand a yeast host that is auxotrophic for a metabolite which is essential to cell growth, and on the other hand a plasmid which enables this auxotrophy to be complemented.

The interferon variants according to the invention may be used in all the applications of natural interferons, such as, for example, the production of antiviral, immunomodulatory, anti-inflammatory and antitumor medicaments. They may also be used as immunogens for inducing the production of anti-type I interferon antibodies.

In addition, the trophoblastin variants obtained according to the invention (these variants are hereinafter designated by the general term APrT) are, apart from the general applications of type I interferons mentioned above, used more specifically for the production of antiluteolytic medicaments as well as of products intended for improving the survival of embryos when they are transplanted, and for the production of reagents permitting diagnosis of the viability of embryos at an early stage of their development.

According to a preferred embodiment of the present invention, APrT is used for the treatment of herds and flocks, in order to improve their fertility.

According to another preferred embodiment of the present invention, APrT is used for the treatment of embryos when they are transplanted, in the various techniques of reproduction of breeding animals involving embryo transfer, especially those associated with cryo-preservation, with in vitro fertilization, with embryo cloning and with embryo transgenesis.

According to yet another preferred embodiment of the present invention, APrT is used for the production of reagents and kits permitting the diagnosis of viability of embryos at an early stage of their development.

Such a diagnosis is based on the assay of the trophoblastin produced by the embryos. This assay can be, for example, performed by immunological methods; in this case, APrT may be used as an immunogen for the production of antibodies, or as an antigen, in competitive type methods. The trophoblastin produced by embryos may also be quantified by its antiviral activity; APrT may be used as a standard of antiviral activity in such an assay.

The immunological properties of APrT may also be turned to good account in order to induce the appearance of anti-trophoblastin antibodies in an animal in which it is desired to produce infertility.

The subject of the present invention is also a method for purifying APrT from culture medium of yeasts that produce it, in which method the APrT is purified by chromatography (for example of the DEAE type) on an anion exchange column with a three-step elution:
  a KCl gradient from 0 to 0.135M
  an isocratic phase at approximately 0.135M KCl
  a KCl gradient from 0.135M to 0.5M, the APrT being collected at between 0.135 and 0.3M KCl.

APrT may also be purified by reverse-phase chromatography, or by affinity chromatography, using anti-trophoblastin antibodies.

BRIEF DESCRIPTION OF THE DRAWINGS

FIG. 1 shows the amino acid sequence of isoforms of tropholastin beginning with the cysteine residue at position 1 and ending with the proline residue at position 172.

DETAILED DESCRIPTION

Figure 2A:
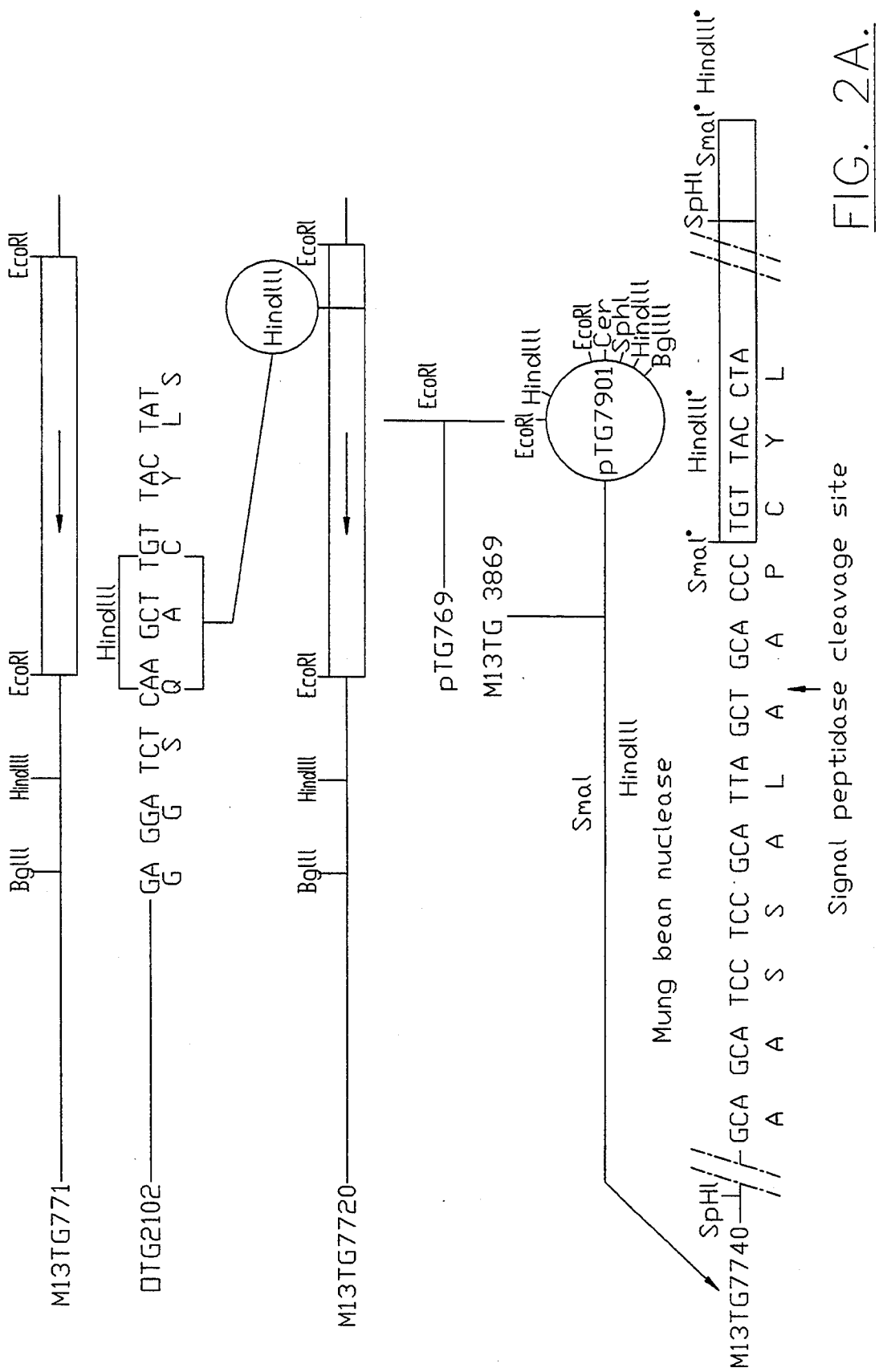
FIG. 2(A) and 2(B) are a schematic summarizing the protocol for obtaining the pTG7908, pTG7904, and pTG7941 plasmids.

A better understanding of the invention will be gained from the further description which follows, which relates to examples of preparation of variants of type I interferon according to the invention.

It is, however, self-evident that these examples are given only by way of illustration of the subject of the invention and in no way constitute a limitation thereof.

The antisense strand of trophoblastin, carried by the single-stranded vector M13TG771, is represented below in line I, and the oligonucleotide OTG2102 is represented in line II; the stars (*) represent the mismatches which will cause the desired mutations.

Line I:  CT CCT AGA GAC CCA ACA ATG GAT A
Line II: GA GGA TCT CAA GCT TGT TAC CTA T.
                      *   *    *

The vector M13TG7720 is thereby obtained. The point mutations which have been introduced into the coding sequence induce the replacement of the amino acids leucine at position -2 and glycine at position -1 of the precursor of trophoblastin by glutamine and alanine, respectively. M13TG7720 is then digested with EcoRI, and the EcoRI DNA fragment coding for the mutated precursor of trophoblastin is inserted into the vector pTG769 (described in Patent Application EP 0,258,118) digested beforehand with EcoRI. The vector pTG7901 is thereby obtained.

Moreover, in order to produce trophoblastin in yeast, the DNA fragment coding for trophoblastin must be placed under the control of a yeast promoter. For this purpose, the vector M13TG3841 is used, this vector being described in the PCT patent application filed on Apr. 28, 1990, the file number of which is FR90/00,306, and containing, in particular:
   the promoter of the gene coding for the alpha 1 factor (MFalpha1); signal peptide of the precursor of the alpha 1 factor; and
   the pro sequence of MFalpha1.

An SmaI restriction site is created between the second and the third codon of the pro sequence of MFalpha1 by directed mutagenesis, using the Amersham kit and oligonucleotide OTG2072 whose sequence is as follows: TCCGCATTAGCTGCTCCCGGGAACACTACAACAGAA.

The antisense strand of the prepro sequences of MFalpha1, carried by the vector M13TG3841, is represented below in line I, and the oligonucleotide OTG2072 is represented in line II; the stars (*) indicate the mismatches which will cause the desired mutations.

Line I  AGG CGT AAT CGA CGA GGT CAG TTG TGA TGT TGT CTT
Line II TCC GCA TTA GCT GCT CCC GGG AAC ACT ACA ACA ACA
                          *   * *
                          SmaI

EXAMPLE 1

Construction of the plasmid for expression of the Ala-Pro variant of ovine trophoblastin in yeast (pTG7908)

The DNA sequence coding for the precursor of ovine trophoblastin, the latter being as described in PCT Application WO 89/08,706 (see also FIG. 1), is cloned in the form of an EcoRI fragment into the vector M13TG131 described in the paper by M. P. KIENY et al., Gene (1983) 26:91. The vector M13TG771 is thereby obtained. In order to be able to isolate the fragment coding for the mature protein, that is to say the DNA fragment without the signal sequence, a HindIII site is created at the 5' end of the mature sequence of the protein by directed mutagensis, using the AMERSHAM kit and the oligonucleotide OTG2102, the sequence of which is as follows: GAGGATCTCAAGCTTGTTACCTAT.

Vector M13TG3869 is thereby obtained. The point mutations which have been introduced into the coding sequence induce the replacement of glycine by valine.

The vector pTG7901 is digested with HindIII to liberate the HindIII DNA fragment coding for mature trophoblastin, which is then treated with mung bean nuclease. This fragment is inserted into the vector M13TG3869 digested beforehand with SmaI. The vector M13TG7740 is thereby obtained, which vector contains, in sequence and in frame:
   the MFalpha1 promoter,
   the pre sequence of MFalpha1, followed by the first two codons of the pro sequence, that is to say those coding for the amino acids alanine and proline, and
   the DNA fragment coding for ovine trophoblastin.

The SphI DNA fragment derived from the vector M13TG7740, containing the MFalpha1 promoter, the pre sequence followed by the alanine and proline codons and the DNA sequence coding for mature trophoblastin, is inserted into the yeast vector pTG3828 (described in the PCT patent application the file number of which is FR90/00,306) digested beforehand with SphI. Plasmid pTG7908 is thereby obtained.

By performing directed mutagenesis of the vector M13TG7740, using the Amersham kit as described above and the oligonucleotide OTG2643, replacement of the sequence coding for the N-terminal extension Ala-Pro by a sequence coding for Ala-Gly is obtained. An SphI fragment of the vector M13TG7745 obtained in this manner is inserted, as described above, into plasmid pTG3828; the resulting plasmid is designated pTG7941.

Figure 2B:
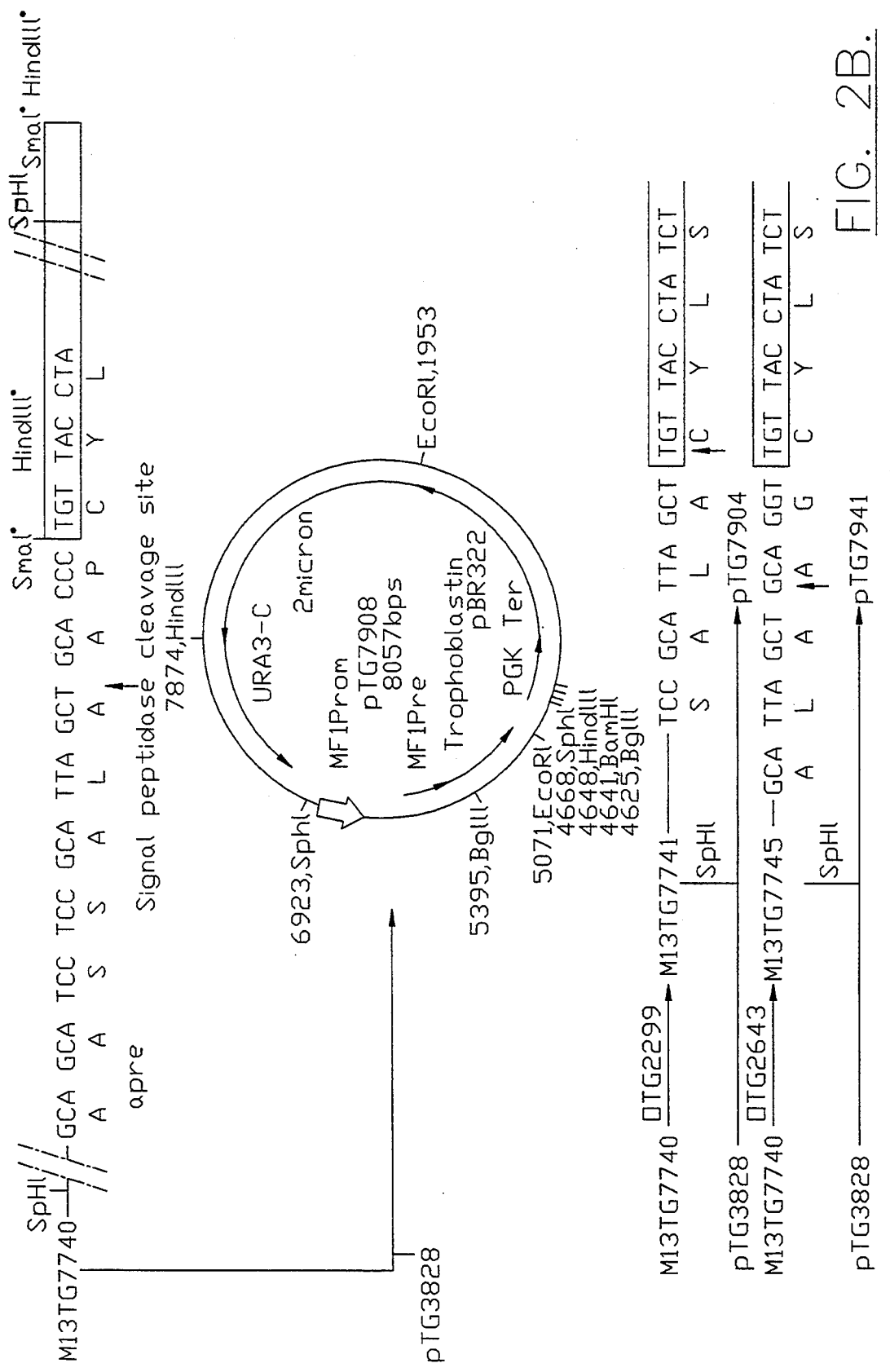

A plasmid designated pTG7904, lacking the sequence coding for the dipeptide Ala-Pro, was also constructed by directed mutagenesis of M13TG7740, by means of the oligonucleotide OTG2299 and insertion of an SphI restriction fragment into pTG3828. FIGS. 2A and 2B summarize the protocol for obtaining pTG7908, pTG7904 and pTG7941.

EXAMPLE 2

Production of the variant Ala-Pro-trophoblastin by yeast

A yeast strain of the species *Saccharomyces cerevisiae*, of genotype MATalpha, ura3-251,-373,-328, leu2-3,-112,his3,pep4-3, is transformed with plasmid pTG7908 by the lithium acetate method [H. ITO et al., J. Bacteriol. (1983) 153], and the uracil prototrophs (Ura+) are selected on a YNBG medium (14 g/l of Yeast Nitrogen Base, 10 g/l of glucose) with the addition of 10 g/l of casamino acids.

To compare the level of expression of the different variants encoded by the plasmids described in Example 1, clones of cells transformed with the plasmids were cultured in flasks at 30° C. to an $OD_{600}$ of 8 to 10 units, in order to determine the production of trophoblastin in the culture supernatants.

The production of recombinant trophoblasin by yeasts transformed, respectively, with plasmids pTG 7904, pTG 7908 and pTG 7941 was evaluated by acrylamide gel electrophoresis, staining with Coomassie blue and comparison with a standard protein preparation (PHARMACIA).

The results are illustrated in the following table.

TABLE I

| Plasmid | Recombinant trophoblastin (mg/l/$OD_{600}$) |
|---------|---------------------------------------------|
| pTG 7904 | 0.06 to 0.25 |
| pTG 7908 | 2 to 2.5 |
| pTG 7941 | 1 to 1.5 |

These results show that the presence of the N-terminal extension of 2 amino acids brings about a substantial increase (from 4- to 10-fold) in the production of recombinant trophoblastin by yeast.

The variant Ala-Pro-trophoblastin is produced by "Fed-Batch" in a BIOLAFFITE 20-L fermenter. 12 l of Käppeli medium D [A. FICCHTER et al., Adv. Microbial. Physiol. (1981), 22, 123–183], concentrated 1.5-fold and containing 10 g/l of glucose and HY Case SF (sold by SHEFFIELD), are inoculated with 400 ml of a preculture of a yeast clone transformed with pTG9708. This preculture is prepared in an Erlenmeyer at 30° C. on a YNBG selective medium. Before fermentation is started up, the $OD_{600}$ of the medium thus inoculated is 0.2. Fermentation is carried out at 30° C., at a pH of 4.5 controlled by the addition of 10% ammonia solution, and at a partial pressure of oxygen corresponding to 30% of the saturation pressure, held constant by regulation of the agitation. When all the glucose has been consumed, the $OD_{600}$ is measured (OD of start of feeding), and feeding with glucose in exponential steps of 3 hours is begun, knowing that the specific growth rate ($\mu$) is 0.1 hour$^{-1}$ and that the quantity of glucose added (QS) is 0.045 g/h/OD. Fermentation is stopped when $ODe_{600} = 100$, and harvesting is carried out by centrifugation at 5000 g. 13 l of culture supernatant containing large quantities of the variant Ala-Pro-trophoblastin are thereby obtained.

EXAMPLE 3

Purification of the variant Ala-Pro-trophoblastin from culture supernatants

On a semi-preparative scale

The yeast culture supernatants are centrifuged, then concentrated and dialyzed against 0.05M Tris-HCl buffer (pH 8.2) in an ultrafiltration cell (AMICON) across a FILTRON membrane that retains molecules above 10 kDa. Isolation of the APrT was performed on a semi-preparative scale by high performance liquid chromatography (HPLC) on a semi-preparative TSK DEAE-5PW anion exchanger column (150×21.5 mm) equilibrated with 0.05M Tris-HCl buffer pH 8.2. The flow rate is 4 ml/min. After injection of the sample, elution is performed with a KCl gradient from 0 to 0.135M (0.05M Tris-HCl buffer pH 8.2) for 90 min, followed by an isocratic plateau phase at 0.135M KCl for 30 min and then a second gradient up to 0.5M KCl for 80 min. The elution is monitored by measuring the absorption at 280 nm. The peak corresponding to APrT is identified using an anti(natural trophoblastin) immune serum (the similarity of the immunological properties of APrT and natural trophoblastin is demonstrated below in Example 4), and the corresponding fractions are then collected. The APrT emerges at the end of the isocratic plateau phase, at between 0.135M and 0.25M KCl.

Figure 3A:
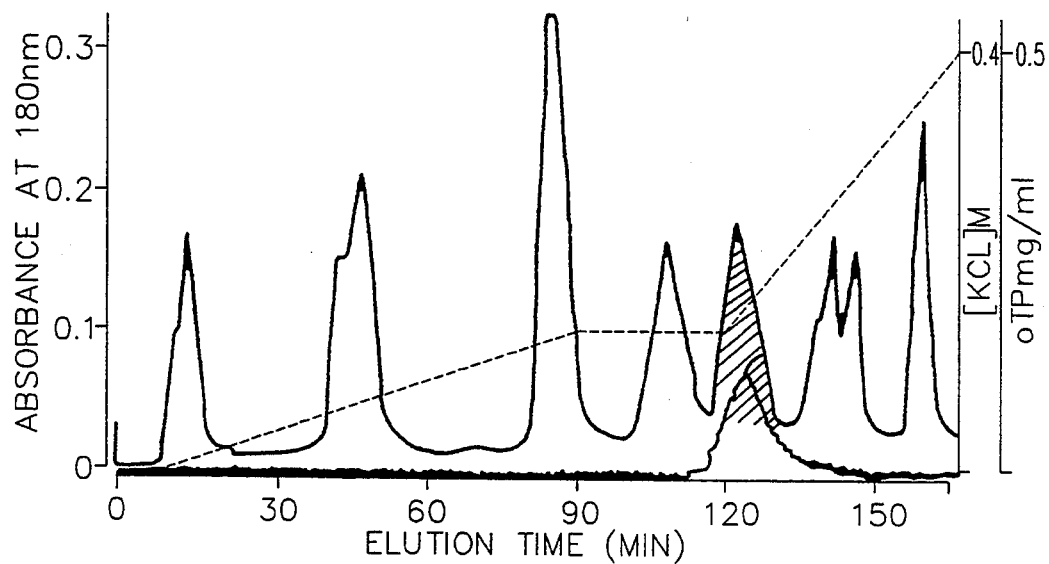
FIG. 3A shows the elution profile obtained in the purification of the Ala-Pro-trophblastin (APrT) variant from yeast culture supernatants the peak corresponding to APrT is shaded.

FIG. 3(a) illustrates the elution profile obtained; the peak corresponding to APrT is shaded.

Figure 4:
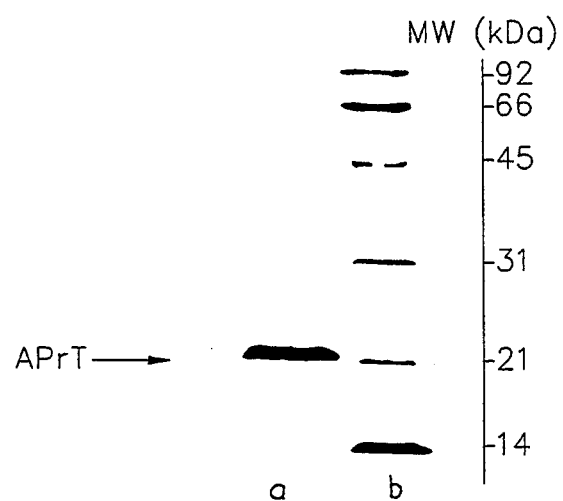
FIG. 4 shows the electrophoretic profile of APrT (lane A) compared to molecular weight (MW) markers (lane B) of varying weights.

The apparent molecular weight of the APrT in polyacrylamide gel electrophoresis in the presence of SDS is approximately 21 kDa. FIG. 4 shows the electrophoretic profile obtained (well a: APrT; well b: molecular weight markers).

Preparative purification

The purification is performed on a preparative TSK DEAE-5PW column (200×55 mm). Elution is performed with a KCl gradient in 0.05M Tris-HCl buffer pH 8.3 at a flow rate of 25 ml/min, under the following conditions:

gradient from 0 to 0.135M KCl for 80 min;
isocratic phase at 0.135M for 40 min;
gradient from 0.135 to 0.5M KCl for 120 min.

Figure 3B:
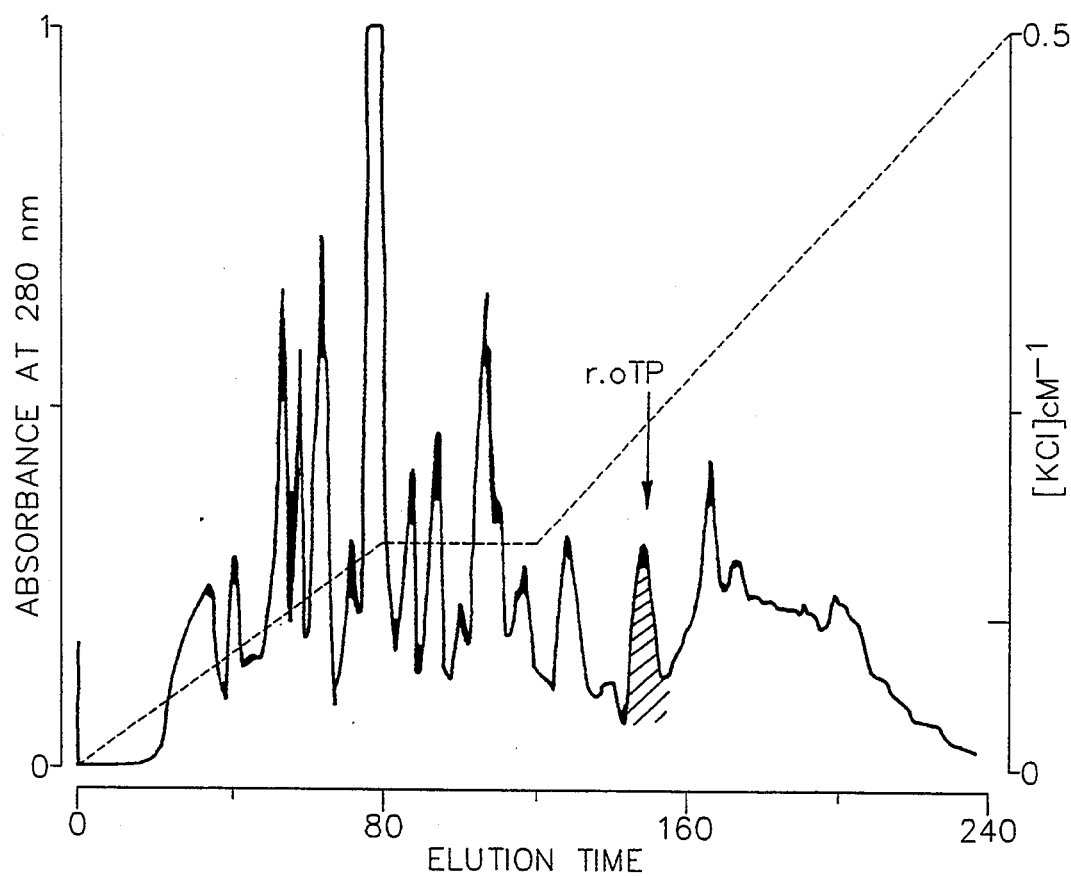
FIG. 3B shows the elution profile obtained in preparative purification of APrT; the peak corresponding to APrT is shaded.

The elution profile is shown in FIG. 3(b). The shaded peak corresponds to APrT.

EXAMPLE 4

Comparison of the immunological properties of APrT with those of natural trophoblastin The existence of immunological cross-reactions between APrT and trophoblastin is evaluated by radioimmunoassay (RIA), using an anti-trophoblastin polyclonal antiserum and an iodine-125-labeled trophoblastin preparation, according to the protocol described in PCT Application 89/08,706.

Figure 5:
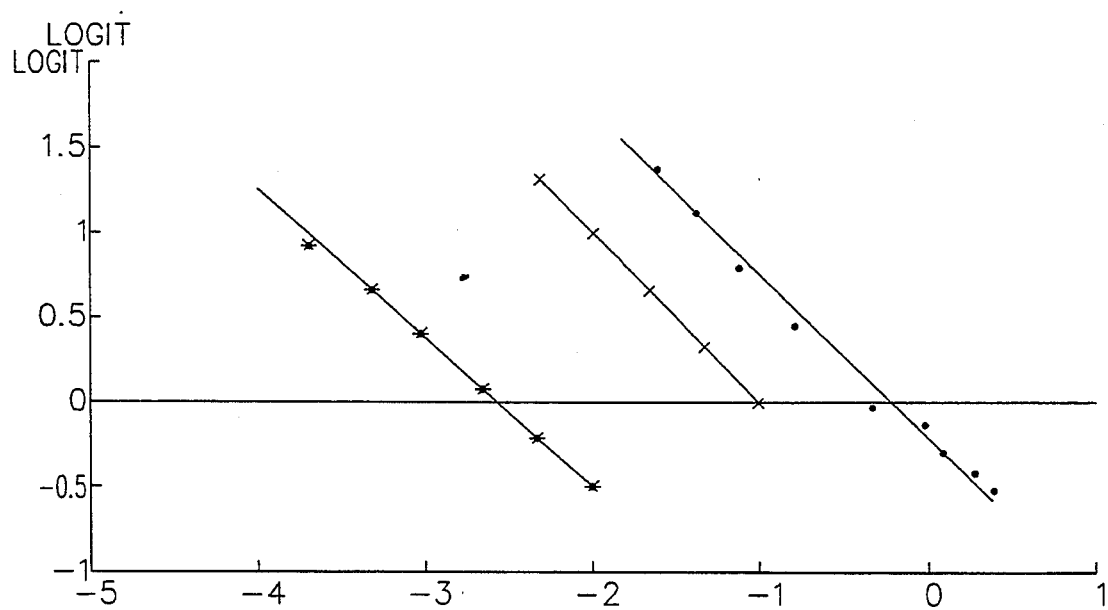
FIG. 5 compares radioimmunossay (RIA) results of APrT and natural trophoblastin, using an anti-trophoblastic polyclonal antiserum and radiolabeled trophoblastin preparations. Solid circles=control solution of natural trophoblastin; x=culture medium of yeast secreting APrT; and *=APrT preparations.

The RIA inhibition curves obtained under these conditions are shown in FIG. 5; the Log of the dilution is plotted as abscissa, and the corresponding Logit=Log (Bo/1-Bo) as ordinate (Bo represents the maximal concentration of bound trophoblastin for a constant concentration of anti-trophoblastin antiserum).

(•) control: purified preparation of natural trophoblastin;
Y= −0.9572X−0.2341
linear regression coefficient=0.9957
(x) culture medium of yeasts secreting APrT (dilutions from 1 to 1/100);
Y= −0.9372X −0.921
linear regression coefficient=0.9996
(*) APrT preparation (dilutions from 1 to 1/4000) obtained as described in Example 1;
Y= −0.9341X−2.41
linear regression coefficient=0.9955

These curves are parallel to one another, thereby demonstrating that the immunological properties of APrT are similar to those of natural trophoblastin.

EXAMPLE 5

Test of antiviral activity

The antiviral activity of APrT is measured according to the protocol described by LA BONNARDIERE and LAUDE [Infection and Immunity, 32, 28–31, (1981)] on MDBK (Madin Darby Bovine Kidney) cells, a calf kidney cell line in the presence of vesicular stomatitis virus.

The results obtained are compared with those obtained using a reference interferon, which is a porcine α interferon having a titer of 1,000 IU, itself calibrated with respect to the human reference standard.

The results of this test of antiviral activity reveal an equivalent activity for the yeast culture medium supernatants ($0.8 \times 10^8$ IU/mg), purified APrT ($0.55 \times 10^8$ IU/mg) and natural trophoblastin ($0.7 \times 10^8$ IU/mg) (the quantity of trophoblastin is determined by radioimmunoassay).

EXAMPLE 6

IN vivo demonstration of the antiluteolytic activity of APrT

Animals and hormone treatment

The experiment was carried out on 30 Préalpes-du-Sud breed ewes. The estrus cycles are synchronized by means of vaginal sponges impregnated with 300 mg of 17α-acetoxy-9α-fluoro-11β-hydroxyprogesterone (SEARLE, INTERVET). These sponges are left in place for 14 days and, on the day of withdrawal (D14), the ewes are injected intramuscularly with 500 IU of PMSG (pregnant mare serum gonadotrophin); 48 hours later, the ewes begin a new cycle (D0).

Insertion of intrauterine catheters

The ewes are anesthetized and then, by laparotomy at the linea alba, the operator gains access to the uterus and marks the corpora lutea using Indian ink. A sterile catheter (SILASTIC, DOW CORNING) 0.076 mm in internal diameter, 0.165 mm in external diameter and 70 cm in length is equipped with a short sleeve at one of its ends, which enables the catheter to be held in place in the uterine horn, substantially at the uterotubal junction. The opening is closed with a needle crimped to a catgut thread (Laboratoire BRUNEAU). A purse-string suture is performed around the insertion orifice of the catheter, effecting durable positioning of the device. A safety stitch made with a needle crimped to silk (Laboratoire BRUNEAU) attaches the catheter to the broad ligament. The other end is closed with a flax thread, and a loop is made so that the operator, after piercing the abdominal wall on the right-hand side, can take out the catheter by pulling the loop. A SILASTIC check ring was placed 30 cm from the intrauterine end in order to limit the projection of the catheter and to act as a stop inside the abdominal wall. A length of approximately 40 cm is at the disposal of the operator who performs the intrauterine injections A stitch made around the abdominal emergence orifice of the catheter enhances the robustness of the device. The insertions of catheters are performed between the 9th and 11th days of the cycle.

Intrauterine infections

Three groups of ewes were formed: the intrauterine injections begin between the 10th and the 12th day of the cycle, and are performed twice a day over 8 days. The APrT is dissolved in physiological saline containing 50,000 IU/ml of penecillin G and 0.2% BSA (bovine serum albumin). The volume of solution injected is 1 ml.

Group A: This is a control group composed of 10 ewes which receive, twice a day, 1 ml of 0.2% BSA (fraction V, SIGMA) solution in physiological saline (0.9% NaCl) containing 50,000 IU/ml of penecillin G.

Group B: This group is composed of 8 ewes to which 170 μg of APrT have been administered twice daily.

Group C: This group is composed of 4 ewes which receive 80 μg of APrT twice a day.

Group D: 5 ewes receive 340 μg of APrT twice a day.

At the end of the experiment, all the ewes undergo an exploratory laparotomy in order, on the one hand to verify that the catheters have in fact stayed in place, and on the other hand to monitor in each group the presence or absence of corpus luteum (or corpora lutea) marked with Indian ink.

Radioimmunoassay of progesterone

Blood of the animals is drawn from the jugular vein using Vacutainer tubes (BECTON-DICKINSON) without anticoagulant. The serum progesterone concentration is determined by direct radioimmunoassay without extraction, according to the protocol described by HEYMAN et al. [J. Reprod. Fert., 70, 533–540, (1984)]. Tritium-labeled progesterone and a specific anti-progesterone immune serum (PASTEUR INSTITUTE) are used for this assay.

In the control group A, the progesterone concentration in the peripheral blood decreases abruptly in all the ewes from the 14th day, reaching levels below 0.5 ng/ml between the 15th and the 17th day post-estrus. The mean duration of the cycle in this group is 15.2±0.3 days. The administration of 80 μg of APrT per day (group C) does not prolong this duration.

In group B (170 μg/day), a slowing down of the fall in the blood progesterone level compared to group A is seen at the 14th day of the cycle: 7 ewes out of 8 exhibit at this stage progesterone levels above 1 ng/ml (against 4 out of 10 in group A); at the 15th day of the cycle, 5 ewes out of 8 still exhibit progesterone levels above 1 ng/ml (against 2 out of 10 in group A).

In this group, luteolysis is delayed on average by 2 days compared to group A.

In group D, the intrauterine administration of APrT at a dose of 340 μg/day maintains luteal function well beyond the duration of the normal cycle in four ewes out of 5 (25, 32, 45 and 64 days, respectively, in ewes nos. 9037, 9431, 9458 and 9053).

Figure 6:
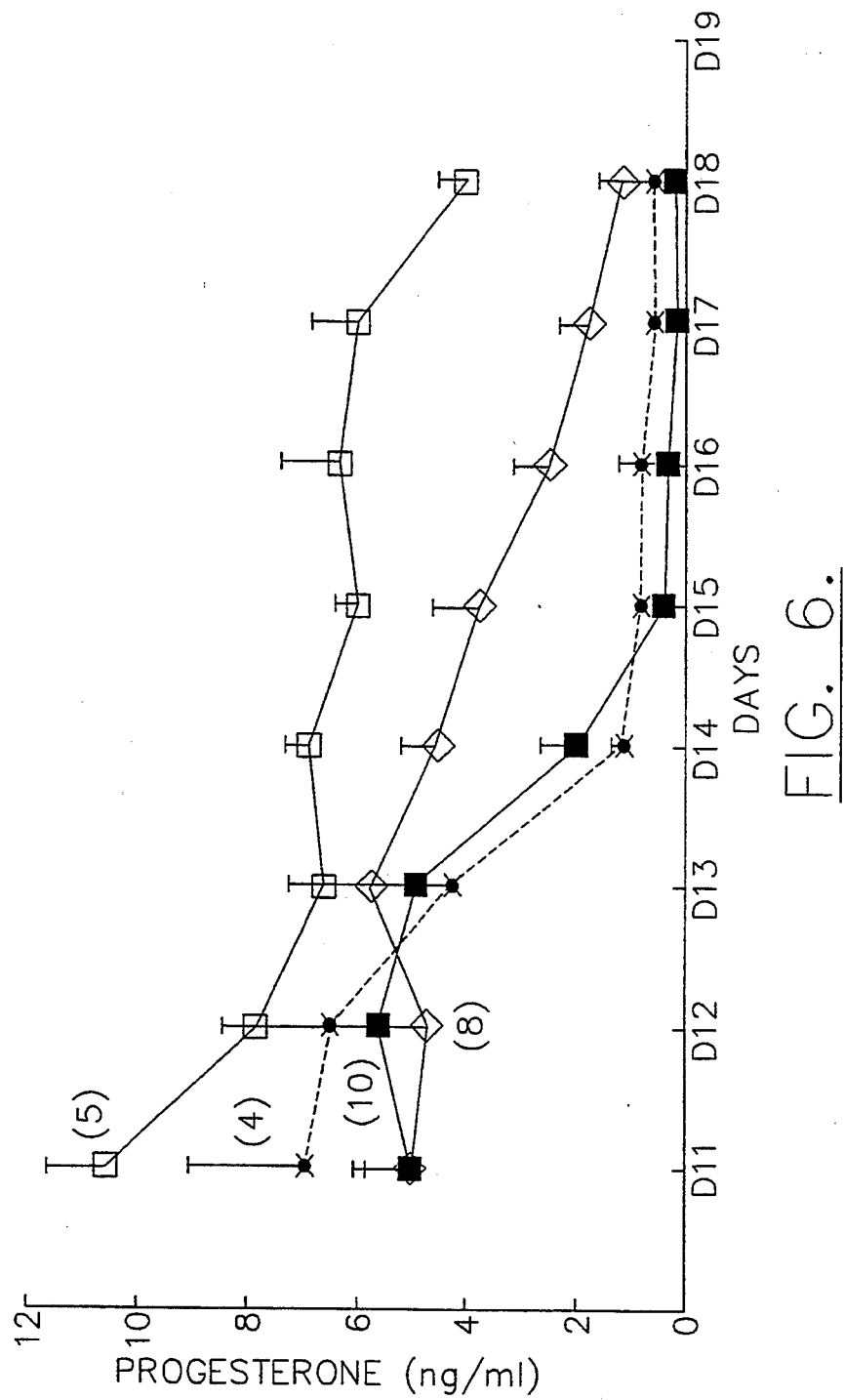
FIG. 6 is a graph comparing the mean profile of progesterone blood levels (ng/ml) in ewes receiving intrauterine injections of APrT, where A=control group; B=170 μg APrT twice daily; C=80 μg APrT twice daily; and D=340 μg APrT twice daily.

The comparative mean profile of progeserone secretion between the different groups, shown in FIG. 6, shows clearly that there is a marked persistence of luteal activity in group D.

(■) Group A
(◇) Group B
(*) Group C
(□) Group D

In addition, during the surgical monitoring by laparotomy, no newly formed corpus luteum was seen in any of the 4 ewes of group D which are mentioned above, showing that the measured blood progesterone level corresponds to the persistence of the cyclic corpora lutea which preceded the injections of APrT.

Possible side effects of APrT were looked for: the mean temperature of the ewes of the test groups was taken daily.

No difference was observed between the temperature of the control animals of group A and that of the animals of the other groups.

More generally speaking, no behavioral disturbance (loss of appetite, and the like) was observed in the animals treated with APrT, compared to the control animals. The same applies to the blood picture (red cells, white cells, platelets) and to the serum transaminase (SGPT) levels.

Intramuscular injections

The same experiment was performed, injecting APrT intramuscularly.

One group of ewes (E) received 2 injections of APrT solution daily (2 mg of APrT/day: 1 mg in the morning, 1 mg at night).

A group of control ewes (F) received injections of a BSA solution (2 mg/day: 1 mg in the morning, 1 mg at night).

The persistence of luteal activity in the animals of group E is similar to that observed in the animals of group D (treated by intrauterine injection).

The only side effect observed is a slight rise in the mean temperature of the animals of group E compared to those of group F. In contrast, no behavioral modification is observed, and neither are modifications of the blood picture and the serum transaminase (SGPT) levels.

Experiments carried out previously showed the antiluteolytic activity of natural trophoblastin, but they did not permit the assertion that trophoblastin sufficed on its own to prevent luteolysis, and had not enabled the role of the different isoforms of trophoblastin to be determined. Now, the experiments described show that the APrT obtained from a single isoform suffices, at suitable doses, to inhibit luteolysis, despite the two additional amino acids of the N-terminal end. Lastly, no apparent sign of proline toxicity is observed.

EXAMPLE 7

Demonstration of the immunosuppressant properties of APrT

These properties were demonstrated by four types of tests enabling different modes of action to be demonstrated:

antimitotic activity, evaluated by the action on the proliferation of mouse, human or sheep lymphocytes;

inhibitory activity with respect to the cytolytic graft rejection reaction, evaluated by means of the in vitro test of the mixed lymphocyte reaction (MLR);

inhibitory activity with respect to the in vivo local graft rejection reaction (local graft versus host reaction);

immunoregulatory activity with respect to the population of NK killer lymphocytes, which are independent of the antigens of the major histocompatibility complex (MHC).

1) Action of APrT on the proliferation of mouse lymphocytes activated with phytohemagglutinin Mouse lymphocytes are obtained from C3H/He or Balb/c mouse spleen after blending in a Potter and washing twice in RPMI 1640 culture medium at 1500 rpm for 10 min. Finally, the isolated lymphocytes are mixed in the same culture medium, to which 10% of fetal calf serum (FCS) is added, at a final concentration of $5 \times 10^6$ cells/ml. The culture medium is composed of 500 ml of RPMI 1640 (GIBCO)+5 ml of penicillin G/streptomycin (GIBCO)+5 ml of 7.5% sodium bicarbonate (GIBCO)+5 ml of glutamine.

100 µl per well of culture medium containing $6 \times 10^5$ lymphocytes, activated with 5 g/ml of phytohemagglutinin (PHA) (WELLCOME), are incubated with 100 µl of an APrT solution at a concentration of 3 µg/ml ($\simeq 10^8$ IU/mg), or 100 µl of culture medium (control), in 96-well microtest plates at 37° C. in an air/$CO_2$ (95%/5%) atmosphere for 48 h.

Lymphocyte proliferation is evaluated by measuring the incorporation of tritiated thymidine. 25 µl of [$^3$H] thymidine (0.04 mCi/ml) are added to each well, and the cells are harvested 24 h later and deposited on filters (Glass Microfibre Filters-GFM-WHATMAN). After drying, the filters are placed in tubes to which 1 ml of scintillation fluid (ECONFLUOR) is added. The radioactivity is measured in a $\beta$-radiation counter (BECKMAN).

Figure 7:
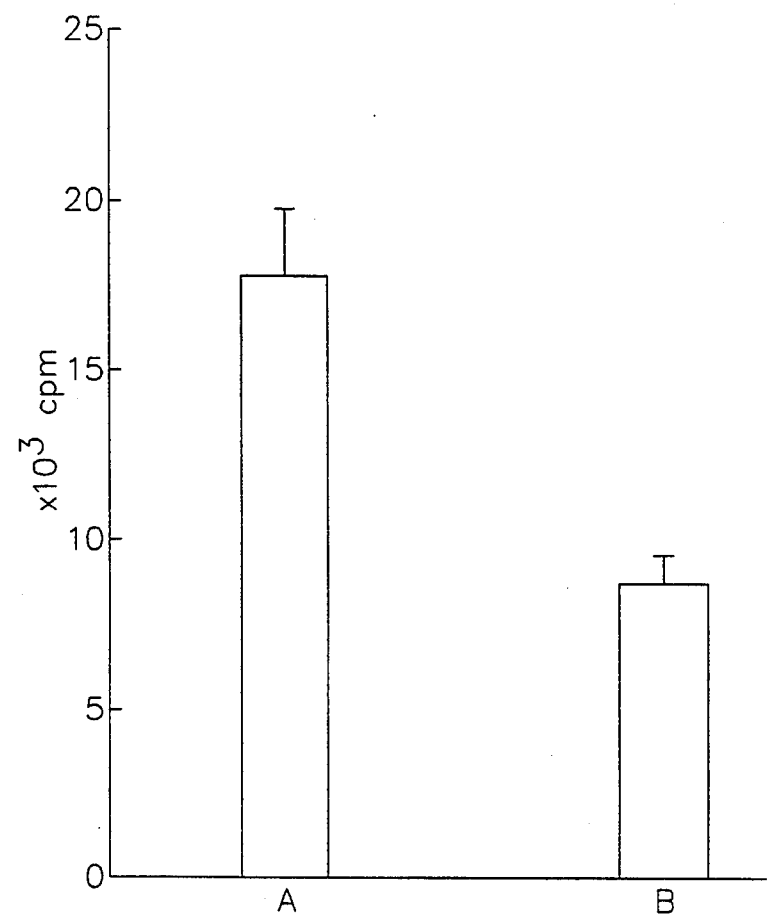
FIG. 7 graphs the inhibition of mouse lymphocyte proliferation by APrT as measured by the incorporation of tritiated thymidine by lympnocytes, where A=control (no APrT) and B=APrT.

The results are illustrated in FIG. 7, which shows that APrT inhibits very markedly (55%) the proliferation of mouse lymphocytes treated with PHA.

A: Control
B: APrT

The radioactivity in cpm is plotted as ordinate. In the presence of human or sheep lymphocytes activated with phytohemagglutinin A (PHA), APrT likewise inhibits lymphocyte replication. This inhibition does not result from a cytotoxic effect of APrT, since cell viability is not affected by APrT, which is shown by incubating the lymphocytes in the presence of trypan blue or of $^{51}$Cr.

2) Action of APrT on a mixed lymphocyte reaction

The mixed lymphocyte reactions are carried out by incubating, per well, 150 µl of culture medium containing $5 \times 10^8$ C3H/He responding cells per ml with $5 \times 10^6$ isogeneic or allogeneic stimulator cells irradiated at 1,800 rads/ml.

C3H/He mouse cells are used for the isogeneic reaction and Balb/c mouse cells for the allogeneic reaction. 100 µl of APrT at a concentration of 3 µg/ml ($10^8$ IU/mg), or of culture medium (control), is added per well in 96-well microtest plates (FALCON 3072) at 37° C., and the cultures are left under an air/$CO_2$ (95%/5%) gaseous atmosphere for 4 days.

Lymphocyte lysis by the cytotoxic lymphocytes produced during the mixed lymphocyte reaction is evaluated by measuring the incorporation of tritiated thymidine. 25 μl of [³H] thymidine are added 24 h before sampling lymphocytes and depositing them on filters. Measurement of the radioactivity of the filters is performed in a scintillation counter.

Figure 8:
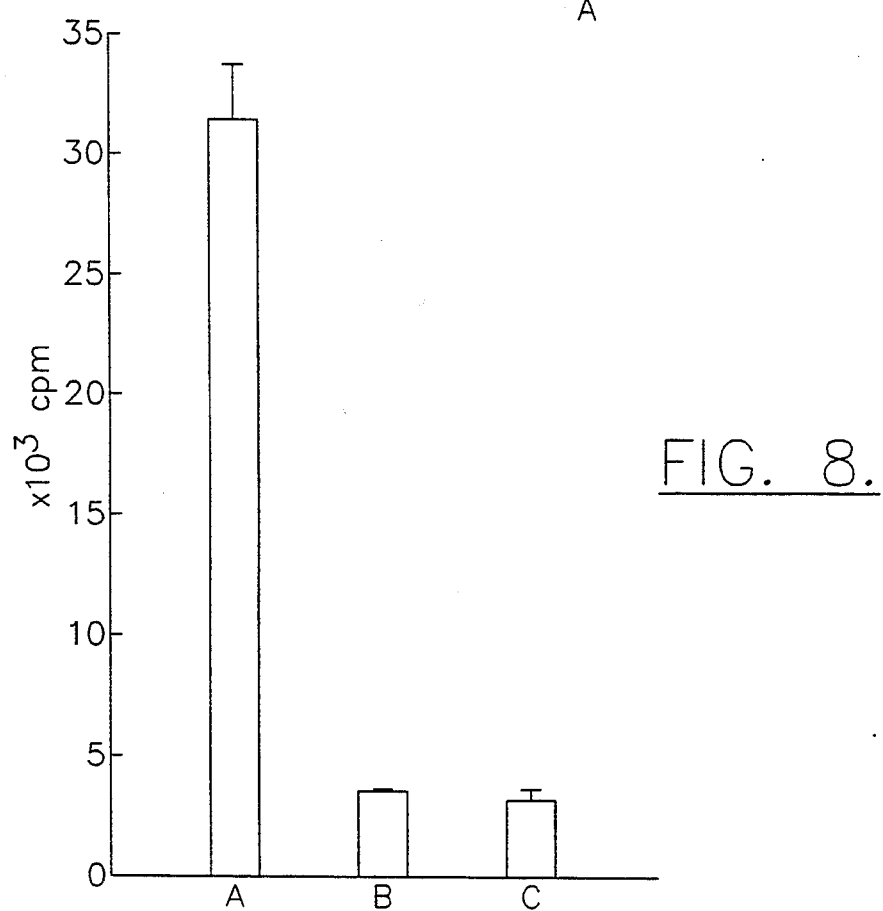
FIG. 8 is a graph comparing the effects of APrT and natural trophoblastin on lymphocyte lysis in an in vitro mixed lymphocyte reaction test, where A=control (no trophoblastin), B=natural trophoblastin, and C=APrT. Lymphocyte lysis was assessed by measuring the incorporation of tritiated thymidine by lymphocytes.

The results are shown in FIG. 8:
A: Control
B: Natural trophoblastin
C: APrT

The radioactivity in cpm is plotted as ordinate.

In two-way culture of lymphocytes originating from two mouse strains (Balb/c and C3H/He), APrT inhibits to the extent of 90% the lysis of mouse lympho-cytes by the cytotoxic cells (CTL) produced.

3) Local graft rejection reaction

APrT in the proportion of 2 μg/ml is added to a suspension of allogeneic spleen cells originating from Balb/c mice, which is injected into the plantar pads of a hind foot of $F_1$ (Balb/b×$B_6$) recipient mice.

The other hind foot, used as a control, is injected with the spleen cells, but without APrT. The popliteal lymphocytic ganglia are removed 4 to 6 days later (depending on the group of mice) and weighed. Cells of these ganglia are removed and activated with PHA; the incorporation of [³H] thymidine in these cells is measured.

Figure 9A:
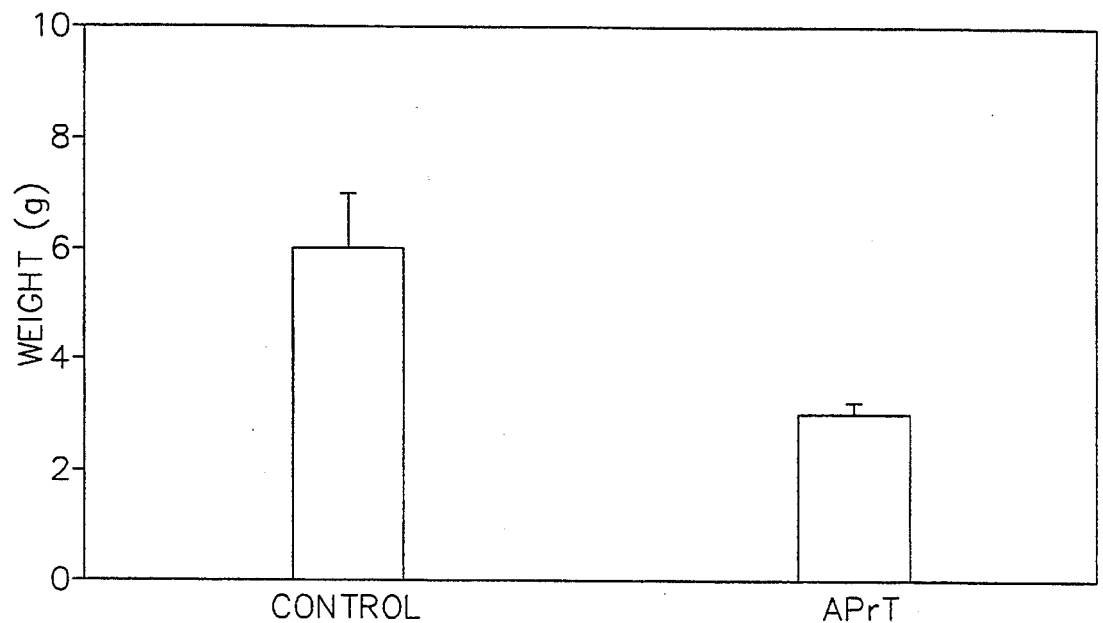
FIG. 9A compares the weight of the popliteal lymphocytic ganglia of mice following injection into the plantar pads of a suspension of allogenic spleen cells containing APrT (APrT), or injection of a control suspension containing only allogenic spleen cells (control).
Figure 9B:
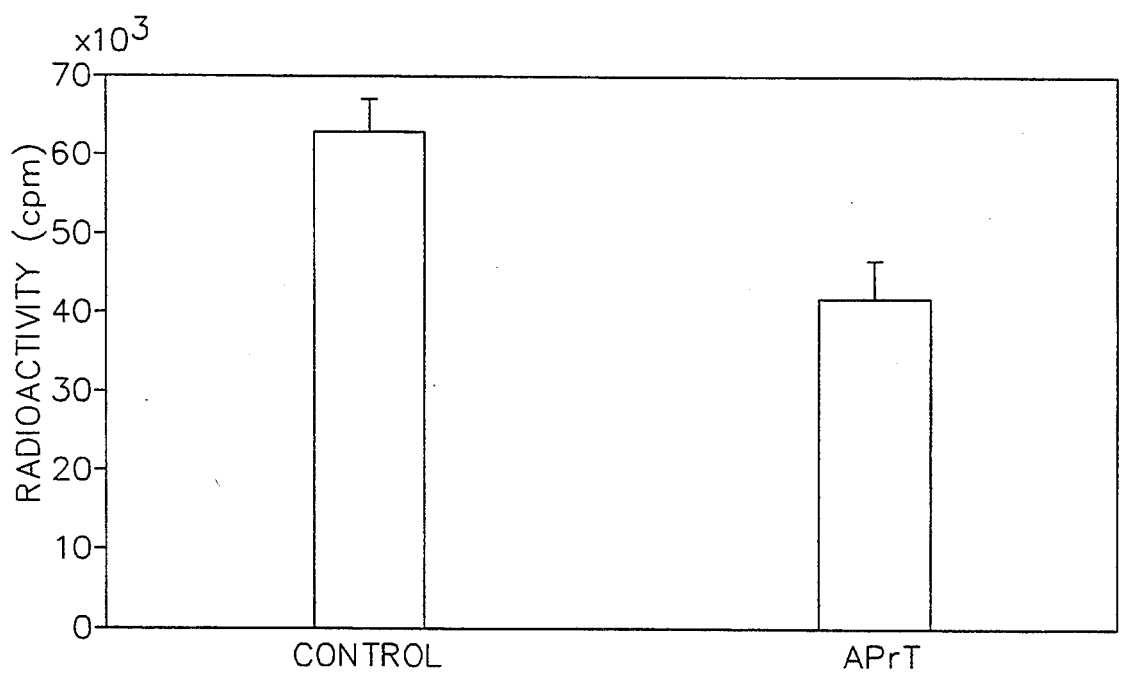
FIG. 9B compares the incorporation of tritiated thymidine in cells originating from the popliteal ganglia of mice following injection of a suspension of allogenic spleen cells containing APrT (APrT), or injection of a control suspension containing only allogenic spleen cells (control).

The results are shown in FIGS. 9(a) and 9(b), which show that the weight of the lymphatic ganglia in the cells treated with APrT is decreased compared to the control cells (FIG. 9a), and that the incorporation of tritiated thymidine in the cells originating from the popliteal ganglia of the feet treated with APrT is also lower than in the control cells (FIG. 9b.

These results show that APrT inhibits in vivo the graft rejection reaction, even in a species (mouse) very distant from the ovine species.

4) Action of APrT on cell lysis by NK cells

K562 cells (human erythroleukemic line) are centrifuged for 10 min at 1,800 rpm, and 0.5 ml of $^{51}Cr$ is deposited on the pellet. After 1 h of incubation at 37° C. in 5% $CO_2$/95% air, the cells are washed three times in RPMI culture medium and resuspended in the same culture medium at a concentration of $2 \times 10^5$ cells/ml.

Three types of incubation in microtitration plates at 37° C. in an air/$CO_2$ (95%/5%) atmosphere are carried out in parallel:

100 μl of labeled K562 cells+100 μl of human lymphocytes 50 to 100 times more concentrated+100 μl of APrT at a concentration of 3 μg/ml ($10^8$ IU/mg), or of culture medium (control), enable the radioactive proteins of the experimental medium (exp. rad. prot.) to be determined;

100 μl of labeled K562 cells+200 μl of 4N HCl enable the radioactive proteins of the total medium (tot. rad. prot.) to be evaluated;

100 μl of labeled K562 cells+200 μl of culture medium enable the radioactive proteins of the natural medium (nat. rad. prot.) to be determined.

After 4 h of incubation, 100 μl of supernatant are sampled from each well, and the radioactivity due to the release of $^{51}Cr$-labeled proteins into the medium is counted in cpm in a gamma-radiation counter.

The results are expressed as the mean percentage cell lysis of samples, and calculated according to the following formula:

$$\% \text{ lysis} = \frac{\text{cpm exp. rad. prot.} - \text{cpm nat. rad. prot.}}{\text{cpm tot. rad. prot.} - \text{cpm nat. rad. prot.}}$$

Figure 10:
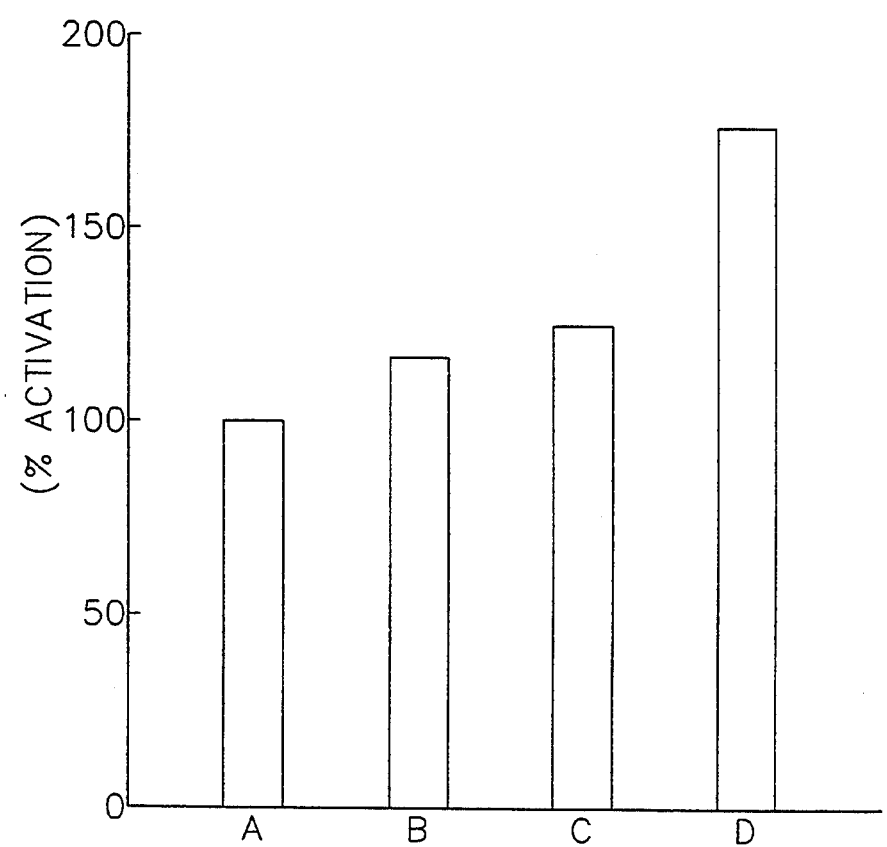
FIG. 10 is a graph comparing the percentage of lysis of human erythroleukemic cells by human lymphocytes in the presence of APrT (B), IFN-alpha (C), and IFN-gamma (D), and the lysis obtained in a control (A) without added interferons.

FIG. 10 shows the results obtained:

A: Control
B: APrT
C: IFN-alpha
D: IFN-gamma

It is hence clearly apparent that APrT activates the cell lysis of K562 target cells by NK cells.

This activation of cell lysis by NK cells is similar to that observed using class I human α interferon, and less than that of the reference human γ interferon.

As is apparent from the foregoing, the invention is in no way limited to those modes of implementation, embodiments and modes of application which have just been described more explicitly; it covers, on the contrary, all variants which may occur to the specialist in the field, without departing from the scope or compass of the present invention.

We claim:

1. A cassette for the expression in yeast of a variant of type I interferon having a formula selected from the group consisting of: Ala-Pro-$R_0'$ (IV) and Ala-Gly-$R_0'$ (V), wherein $R_0'$ is the amino acid sequence of an IFN selected from the group consisting of IFN-alphaII and IFNs of the trophoblastin class;
   said cassette comprising
   a first DNA fragment coding for said variant;
   a second DNA fragment coding for a signal peptide selected from the group consisting of yeast α factor precursor signal peptide and yeast β-1,3-glucanase precursor signal peptide, said second DNA fragment being linked to the end of the first DNA fragment; and
   a promoter enabling said DNA fragments to be expressed in yeast.

2. The expression cassette of claim 1, wherein the first DNA fragment codes for a variant of type I interferon selected from the group consisting of:
   an interferon of formula ($X_a$) in which $R_5$ is arginine, $R_6$ is lysine, $R_{35}$ is aspartic acid, $R_{44}$ is glutamic acid, $R_{48}$ is leucine, and $R_{49}$ is glutamine;
   an interferon of formula ($X_b$) in which $R_5$ is glutamic acid, $R_6$ is arginine, $R_{35}$ is lysine, $R_{44}$ is glutamic acid, $R_{48}$ is aspartic acid, and $R_{49}$ is leucine;
   an interferon of formula ($X_c$) in which $R_5$ is glutamine, $R_6$ is arginine, $R_{35}$ is aspartic acid, and $R_{44}$ is aspartic acid; and
   an interferon of formula ($X_d$) in which $R_5$ is glutamine, $R_6$ is arginine, $R_{35}$ is aspartic acid, $R_{44}$ is glutamic acid, $R_{48}$ is leucine, and $R_{49}$ is glutamine.

3. A cassette for the expression in yeast of a variant of type I interferon having a formula selected from the group consisting of: Ala-Pro-$R_0''$ (VI) and Ala-Gly-$R_0''$ (VII), wherein $R_0''$ is the amino acid sequence of a mature form of an isoform of ovine trophoblastin;
   said cassette comprising:
   a first DNA fragment coding for said variant;
   a second DNA fragment coding for a signal peptide selected from the group consisting of yeast α factor precursor signal peptide and yeast β-1,3-glucanase precursor signal peptide, said second DNA fragment being linked to the 5' end of the first DNA fragment; and
   a promotor enabling said DNA fragments to be expressed in yeast.

4. The expression cassette of claim 3, wherein $R_0''$ is selected from the group consisting of the amino acid sequences of a mature form of ovine trophoblastin isoform $T_1$, $T_2$, $T_3$, $T_4$ and $T_5$.

5. The expression cassette of claim 3, wherein said first DNA fragment codes for a variant in which $R_0''$ is an amino acid sequence of an isoform of ovine trophoblastin, beginning with the cysteine residue at position 1 and ending with the proline residue at position 172, in which:

$R_5$ is a glutamic acid, glutamine or arginine residue;
$R_6$ is an arginine or lysine residue;
$R_{35}$ is a glutamic acid or aspartic acid residue;
$R_{44}$ is a glutamic acid or aspartic acid residue;
$R_{48}a$ is a leucine or aspartic acid residue; and
$R_{49}$ is a leucine or glutamine residue.

* * * * *

UNITED STATES PATENT AND TRADEMARK OFFICE
CERTIFICATE OF CORRECTION

PATENT NO. : 5,378,823

DATED : January 3, 1995

INVENTOR(S) : Jacques Martal et al.

It is certified that error appears in the above-identified patent and that said Letters Patent is hereby corrected as shown below:

On the Title page, item [56] References Cited;
  in the publication by K. M. Zsebo et al., the word "Direction" should be -- Directed --.

Column 1, lines 35-36, "isofoms" should be
  -- isoforms --.

Column 6, line 49, "tropholastin" should be
  -- trophoblastin --.

Column 6, line 52, "FIG. 2(A) and 2(B)" should be
  -- FIG. 2A and 2B --.

Column 6, line 57, a semicolon -- ; -- should be inserted after "supernatants".

Column 6, line 65, "radioimmunossay" should be
  -- radioimmunoassay --.

Column 7, line 10, "lympnocytes" should be
  -- lymphocytes --.

Column 8, line 30, before "signal" the following should be added -- the pre sequence of MFalpha1 coding for the --.

Column 10, line 10, "ODe$_{600}$" should be -- OD$_{600}$ --.

UNITED STATES PATENT AND TRADEMARK OFFICE
CERTIFICATE OF CORRECTION

PATENT NO. : 5,378,823

DATED : January 3, 1995

INVENTOR(S) : Jacques Martal et al.

It is certified that error appears in the above-identified patent and that said Letters Patent is hereby corrected as shown below:

Column 11, line 45, "IN" should be -- In --.

Column 12, line 17, "infections" should be -- injections --.

Column 14, line 25, "5 g/ml" should be -- 5 µg/ml --.

Column 16, line 30, -- 5' -- should be inserted before "end".

Column 16, line 44, "is" (first occurrence) should be deleted.

Column 16, line 63, "promotor" should be -- promoter --.

Column 16, line 68, "$T_1$, $T_2$, $T_3$, $T_4$ and $T_5$" should be -- T1, T2, T3, T4 and T5 --.

Column 18, line 5, "a" (first occurrence) should be deleted.

Signed and Sealed this

Second Day of May, 1995

Attest:

BRUCE LEHMAN

Attesting Officer

Commissioner of Patents and Trademarks